(12) United States Patent
Vlachos et al.

(10) Patent No.: US 11,918,661 B2
(45) Date of Patent: Mar. 5, 2024

(54) THERMALLY-MODULATED ULTRASOUND CONTRAST AGENTS

(71) Applicant: Purdue Research Foundation, West Lafayette, IN (US)

(72) Inventors: Pavlos P Vlachos, West Lafayette, IN (US); Anastasiia Vasiukhina, West Lafayette, IN (US); Luis Solorio, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 252 days.

(21) Appl. No.: 16/935,308

(22) Filed: Jul. 22, 2020

(65) Prior Publication Data
US 2021/0030898 A1 Feb. 4, 2021

Related U.S. Application Data

(60) Provisional application No. 62/880,936, filed on Jul. 31, 2019.

(51) Int. Cl.
*A61K 49/22* (2006.01)
*A61K 47/42* (2017.01)

(52) U.S. Cl.
CPC ............ *A61K 49/227* (2013.01); *A61K 47/42* (2013.01); *A61K 49/221* (2013.01)

(58) Field of Classification Search
None
See application file for complete search history.

(56) References Cited

U.S. PATENT DOCUMENTS

2017/0274103 A1 9/2017 Wang

FOREIGN PATENT DOCUMENTS

WO WO-2013055791 A1 * 4/2013 ............. A61B 8/085

OTHER PUBLICATIONS

Yoon H., et al., Contrast-enhanced ultrasound imaging in vivo with laser-activated nanodroplets. Med. Phys. 44 (7), Jul. 2017.
Yang L., et al., Phase-Transition Nanodroplets for Real-Time Photoacoustic Ultrasound Dual-Modality Imaging and Photothermal Therapy of Sentinel Lymph Node in Breast Cancer. Scientific Reports, 7:45213, DOI: 10.1038/srep45213, Mar. 24, 2017.

(Continued)

*Primary Examiner* — Jennifer Chin
(74) *Attorney, Agent, or Firm* — Purdue Research Foundation (57) ABSTRACT

The present disclosure relates to a novel nano-droplet composition comprising a fluorocarbon core and a polymeric shell, and the method of using and making the novel nano-droplet composition. The fluorocarbon core and the polymeric shell of the novel nano-droplet form a micelle with a size range of 10-1000 nm. The fluorocarbon core comprises at least one fluorocarbon compound with a formula of $C_nF_{2n+2}$ and n is 5-10. The fluorocarbon compound is substantial in liquid form. And the nano-droplet composition has a temperature profile such that the nano-droplet composition has a temperature range of 20-60° C. throughout a temperature modulation process, and has a temperature of about 37° C. prior to administration to a human, animal, biological cell, or tissue subject.

20 Claims, 6 Drawing Sheets

(56) References Cited

OTHER PUBLICATIONS

Zullino S., et al., From Micro- to Nano-Multifunctional Theranostic Platform: Effective Ultrasound Imaging Is Not Just a Matter of Scale. Molecular Imaging, 1-16, 2018.
Kandadai M., et al., Comparison of Surfactants Used to Prepare Aqueous Perfluoropentane Emulsions for Pharmaceutical Applications. Langmuir. Author manuscript; available in PMC Apr. 6, 2011.
Hallam, K., et al., Laser-activated perfluorocarbon nanodroplets: a new tool for blood brain barrier opening. vol. 9, No. 9., 2018, Biomedical Optics Express 4528.
International Search Report and Written Opinion issued by the ISA/US, Commissioner for Patents, dated Nov. 19, 2020, for International Application No. PCT/US2020/042950; 8 pgs.
Díaz-López, R. et al., The Performance of EPGylated Nanocapsules of Perfluorooctyl Bromide as an Ultrasound Contrast Agent, Biomaterials 31, (2010) 1723-1731; 9 pgs.
Perera, R. H., Ultrasound Imaging Beyond the Vasculature with New Generation Contrast Agents, WIREs Nanomed Nanobiotechnol, vol. 7, (2015) 593-608; 16 pgs.

\* cited by examiner

THERMALLY-MODULATED ULTRASOUND CONTRAST AGENTS

CROSS-REFERENCE TO RELATED APPLICATION

This application claims the priority benefit of U.S. Provisional Patent application No. 62/880,936, filed Jul. 31, 2019, which is incorporated herein by reference in its entirety.

TECHNICAL FIELD

The present disclosure relates to a novel nano-droplet composition comprising a fluorocarbon core and a polymeric shell, and the method of using and making the novel nano-droplet composition.

BACKGROUND

This section introduces aspects that may help facilitate a better understanding of the disclosure. Accordingly, these statements are to be read in this light and are not to be understood as admissions about what is or is not prior art.

Ultrasound (US) is one of the most widely used clinical imaging modalities and is utilized in cardiology and vascular imaging, as well as urology, gynecology, obstetrics and general abdominal imaging. The advantages of US imaging include portability, non-ionizing nature, and high spatial and temporal resolution. Despite its strengths, ultrasound is limited when it comes to imaging small anatomical structures deeper inside the patient's body. Larger penetration depths require the use of low-frequency pulses, which results in low spatial resolution and complicates imaging procedures. Administration of contrast-enhancing substances to patients during US imaging sessions can facilitate improved visualization of anatomical structures and more accurate diagnosis. Moreover, ultrasound contrast agents (UCA) can be utilized to provide therapeutic benefits in US-mediated thrombolysis, tumor ablation, sonoporation, and drug and gene delivery.

Currently, all commercially available UCAs are gas-filled, shell-encapsulated microbubbles that provide contrast enhancement, but suffer from short term stability (<10 minutes) and are restricted to intravascular and cardiac applications due to their large hydrodynamic diameter (1-5 µm). In order to expand application of UCAs to beyond vascular and cardiac imaging, for example in the field of oncology, gas-based nanobubbles (NB) have been developed. While several nanobubble formulations exhibit echogenicity comparable to commercially available microscale bubbles, the circulation times of these NBs remain limited, thus inhibiting their use in tumor imaging or therapeutic applications that require their long-term accumulation in disease regions of interest. Despite attempts to improve gas nanobubble stability by manipulating shell composition, there is still much room for improvement in that aspect.

The stability of nanoscale shell-encapsulated contrast agents can be increased by substituting the gas in their core with liquid perfluorocarbons (PFC) to form nanodroplets. Liquid PFCs are stable, chemically inert compounds with high respiratory gas-dissolving capacity (Riess, 2005). These properties of liquid fluorinated hydrocarbons sparked their use in biomedicine, with PFCs having been used in liquid-assisted ventilation and as artificial red blood cell substitutes. Liquid PFCs are immiscible with aqueous solutions, have high molecular weight and low surface tension due to weak intermolecular forces, which makes nanodroplet-based UCAs significantly more stable than their gas-based counterparts. Nevertheless, as a consequence of the small acoustic impedance mismatch between the liquid PFC core of the particles and the surrounding tissue or biological fluids and incompressibility of the liquid core, the echogenicity of nanodroplets is very low. However, when exposed to acoustic energy of sufficient amplitude, poorly echogenic liquid PFC-based nanodroplets become strongly echogenic gas microbubbles via acoustic droplet vaporization (ADV). But working with acoustically-triggered phase-change droplets is subject to a number of challenges, including the need for high vaporization energy, nonuniformity of activation in polydisperse particle samples, and often having to tailor nanodroplet design to each specific application. Moreover, the circulation half-life of PFC bubbles after ADV is short (on the order of several minutes).

Therefore, there is an unmet need for simple yet highly effective composition and method for significantly increasing the echogenicity of liquid fluorocarbon nanodroplets while preserving the original droplet size and echogenic stability.

SUMMARY

The present disclosure relates to a novel nano-droplet composition comprising a fluorocarbon core and a polymeric shell, and the method of using and making the novel nano-droplet composition.

In one embodiment, the present disclosure provides a nano-droplet composition comprising a fluorocarbon core and a polymeric shell, wherein:
- the fluorocarbon core and the polymeric shell form a micelle with a size range of 10-1000 nm;
- the fluorocarbon core comprises at least one fluorocarbon compound with a formula of $C_nF_{2n+2}$ and n is 5-10;
- the fluorocarbon compound is substantial in liquid form; and
- the nano-droplet composition has a temperature profile such that the nano-droplet composition has a temperature range of 20-60° C. throughout a temperature modulation process, and has a temperature of about 37° C. prior to administration to a human, animal, biological cell, or tissue subject.

DETAILED DESCRIPTION

For the purposes of promoting an understanding of the principles of the present disclosure, reference will now be made to embodiments illustrated in drawings, and specific language will be used to describe the same. It will nevertheless be understood that no limitation of the scope of this disclosure is thereby intended.

In the present disclosure the term "about" can allow for a degree of variability in a value or range, for example, within 10%, within 5%, or within 1% of a stated value or of a stated limit of a range.

In the present disclosure the term "substantially" can allow for a degree of variability in a value or range, for example, within 90%, within 95%, or within 99% of a stated value or of a stated limit of a range.

This disclosure presents a discovery that liquid tetradecafluorohexane (TDFH, or perfluorohexane ($C_6F_{14}$)) nanodroplets stabilized with a shell of bovine serum albumin (BSA) exhibit an unexpected, thermally responsive echogenic behavior that is independent of vaporization. Hence, the present disclosure develops and presents, for the first time, a simple yet effective thermal modulation method for inducing the echogenicity of PFC nanodroplets without triggering a transient phase change. The present disclosure shows that poorly echogenic PFC nanodroplets can be activated outside of the body in a simple, precisely controlled manner via a heat modulation process. Once activated, the particles maintained their enhanced echogenicity for at least 13 hours while retaining their nanoscale size. In this study, heat modulation process was applied to BSA-shelled nanodroplets that were prepared and characterized in terms of structural property, size, echogenicity, and in vitro stability.

In one embodiment, the present disclosure provides a nano-droplet composition comprising a fluorocarbon core and a polymeric shell, wherein:
  the fluorocarbon core and the polymeric shell form a micelle with a size range of 10-1000 nm;
  the fluorocarbon core comprises at least one fluorocarbon compound with a formula of $C_nF_{2n+2}$ and n is 5-10;
  the fluorocarbon compound is substantial in liquid form; and
  the nano-droplet composition has a temperature profile such that the nano-droplet composition has a temperature range of 20-60° C. throughout a temperature modulation process, and has a temperature of about 37° C. prior to administration to a human, animal, biological cell, or tissue subject.

In one embodiment regarding the nano-droplet composition of the present disclosure, wherein the fluorocarbon compound is perfluorohexane ($C_6F_{14}$).

In one embodiment regarding the nano-droplet composition of the present disclosure, wherein the polymeric shell comprises a biocompatible polymeric material, wherein the biocompatible polymeric material may be optionally modified by incorporating various ligands to turn the nano-droplet into a multi-functional agent suitable for targeted diagnostics and therapy.

In one embodiment regarding the nano-droplet composition of the present disclosure, wherein the biocompatible polymeric material comprises synthetic polymers, polysaccharides, proteins, peptides, lipids, nucleic acids, or any combination thereof.

In one embodiment regarding the nano-droplet composition of the present disclosure, wherein the biocompatible polymeric material comprises bovine serum albumin (BSA).

In one embodiment regarding the nano-droplet composition of the present disclosure, wherein the fluorocarbon core comprises at least 90 wt. % of fluorocarbon.

In one embodiment regarding the nano-droplet composition of the present disclosure, wherein the composition is used as an ultrasound contrast agent in an ultrasound imaging process.

In one embodiment regarding the nano-droplet composition of the present disclosure, wherein the nano-droplet micelle maintains a size range between 10-1000 nm and the fluorocarbon compound maintains the liquid form throughout temperature modulation process and the ultrasound imaging process.

In one embodiment regarding the nano-droplet composition of the present disclosure, wherein the nano-droplet composition is capable of providing sufficient ultrasound contrast function for at least 10 minutes.

In one embodiment regarding the nano-droplet composition of the present disclosure, wherein the nano-droplet composition is capable of providing sufficient ultrasound contrast function for 30-780 minutes.

In one embodiment regarding the nano-droplet composition of the present disclosure, wherein the nano-droplet composition has a particle size range of about 50-400 nm.

In one embodiment, the present disclosure provides a method of using any nano-droplet composition of the present disclosure as an ultrasound contrast agent, wherein the method comprises:
  providing any nano-droplet composition comprising a core and a polymeric shell, wherein the fluorocarbon core and a polymeric shell forms a micelle with a size range of 10-1000 nm; and wherein the core is substantial in liquid form;
  subjecting the nano-droplet composition to a temperature modulation process to modulated or enhance the ultrasound signal exhibited by the nano-droplet composition, wherein the temperature modulation process is applied outside a human, animal or biological cell or tissue subject for ultrasound imaging process and can be fully and easily controlled;
  administering the nano-droplet composition that exhibits enhanced ultrasound contrast to the human, animal or biological cell or tissue subject; and
  performing an ultrasound imaging on the human, animal or biological cell or tissue subject.

In one embodiment regarding the method of using any nano-droplet composition of the present disclosure, wherein the nano-droplet composition has a temperature profile such that the nano-droplet composition has a temperature range of 20-60° C. throughout a temperature modulation process, and has a temperature of about 37° C. prior to administration to a human, animal, biological cell, or tissue subject.

In one embodiment regarding the method of using any nano-droplet composition of the present disclosure, wherein the core comprises at least one fluorocarbon compound, wherein the fluorocarbon compound has a formula of $C_nF_{2n+2}$ and n is 5-10; and wherein the fluorocarbon compound is substantial in liquid form.

In one embodiment regarding the method of using any nano-droplet composition of the present disclosure, wherein the fluorocarbon compound is perfluorohexane ($C_6F_{14}$).

In one embodiment regarding the method of using any nano-droplet composition of the present disclosure, wherein the polymeric shell comprises synthetic polymers, polysaccharides, proteins, peptides, lipids, nucleic acids, or any combination thereof.

In one embodiment regarding the method of using any nano-droplet composition of the present disclosure, wherein the biocompatible polymeric material comprises Bovine serum albumin (BSA).

In one embodiment regarding the method of using any nano-droplet composition of the present disclosure, wherein the nano-droplet composition is capable of providing sufficient ultrasound contrast function for at least 10 minutes.

In one embodiment regarding the method of using any nano-droplet composition of the present disclosure, wherein the nano-droplet composition is capable of providing sufficient ultrasound contrast function for 30-780 minutes.

In one embodiment regarding the method of using any nano-droplet composition of the present disclosure, wherein the temperature modulation process comprises a cycle of elevating temperature of the nano-droplet composition above 37° C. first, and cooling temperature to 37° C. or any other temperature below 37° C.

In one embodiment regarding the method of using any nano-droplet composition of the present disclosure, wherein the temperature modulation process comprises a plurality of cycles of elevating and cooling the temperature of the nano-droplet composition to allow the nano-droplet composition to have an optimized external temperature profile as an ultrasound contrast agent.

Materials and Methods

Nanodroplet Formulation and Characterization

BSA-Shelled Tetradecafluorohexane Nanodroplet Formulation

BSA-shelled tetradecafluorohexane (or perfluorohexane ($C_6F_{14}$)) nanodroplets were prepared by combining 250 µl of liquid TDFH (Sigma Aldrich) at −20° C. with 850 µL of 1.4% solution of BSA (Rockland antibodies & assays) in 2 ml glass scintillation vials. The vials were then capped and sealed with Parafilm, and air was removed using a 10 ml syringe. Each vial was then agitated on a VialMix shaker for 135 s (3 consecutive cycles of 45 s) to form the nanodroplets and stored at 4° C. for 30 minutes.

Sample formulations were diluted to the desired concentration with 1×PBS and centrifuged at 500 rcf for 5 min to isolate nano-sized droplets from an initially polydisperse particle population.

Sample formulations were diluted to the desired concentration with 1×PBS and centrifuged at 500 rcf for 5 min to isolate nano-sized droplets from an initially polydisperse particle population.

Nanodroplet structure and sizing Transmission electron microscopy (TEM) was used to provide information about the dry particle size distribution and morphology. The mean hydrodynamic diameter and zeta potential were then measured using dynamic light scattering (DLC). Confocal microscopy was used to directly visualize the nanodroplets before and after heat modulation. Before obtaining the TEM and confocal images as well as DLS size measurements, sample formulations were diluted 1:167.7 with 1×PBS. For DLS zeta potential measurements, nanodroplet samples were diluted 1:167.7 with 1 mM KCl. Dilute particle concentrations were used to minimize multiple scattering and particle-particle interactions during DLS measurements, and to limit the saturation in the fluorescence field during confocal imaging.

The TEM grids were glow-discharged for 30 seconds before sample application. 3 µL aliquots of nanodroplet samples were applied to carbon TEM grids (Carbon film only on 200 mesh, Copper; Ted Pella). The grids were then blotted with filter paper and placed on a sample holder. Images were acquired using a Gatan US1000 2K CCD camera on FEI Tecnai T20 electron microscope equipped with a LaB6 source and operating at 200 kV.

The average hydrodynamic diameter and zeta potential of BSA-TDFH nanodroplets were measured using DLS on a Zetasizer Nano ZS90 (Malvern Panalytical) at 22° C.

The nanodroplets were prepared with fluorescent BSA (Alexa Fluor 594 conjugate). A Zeiss LSM 880 confocal microscope (Carl Zeiss Microscopy, LLC) was used to image the nanodroplets in a microfluidic slide (µ-Slide VI 0.4, Ibidi). The channel was viewed through a 63× oil objective lens (numerical aperture NA=1.4), and illuminated by an Argon laser (561 nm wavelength). The images were obtained at five different Z locations inside the microfluidic channel: Z=0 µm (at the level of the glass), 20 µm, 40 µm, 100 µm and 200 µm above the glass. At each position, a time series of 1000 cycles was recorded, with the pixel dwell time of 0.85 µsec and a scan time of 65 msec. The pixel size was set to 0.11 µm. A heated confocal stage was used to maintain the particles at 37° C. after thermal modulation.

The confocal image series were then processed using image-based probability estimation of displacement (iPED) method to find the average diffusion coefficient of the droplets in the solution. The Stokes-Einstein equation was used to determine the size of the particles based on the measured diffusion coefficient, solution viscosity, and the temperature. The average radii of the nanodroplets were found at each scanning height. The average size of the nanodrops within each sample are found by taking the average size of all scanned levels. The number of the nanodrops at each level are found using an adapted version of the mutual information. Mutual information (MI) is a method for counting moving object based on the cross-correlation of consecutive frames. MI finds the number of particles from the ratio of the height of the cross-correlation peak to the height of the auto-correlation peak for one particle. MI method is designed for cases where all the objects move with the same velocity and does not account for random displacement of objects. However, nanodrops undergo a random (Brownian) motion. Therefore, instead of using the height of the peaks, we used the energy of correlations, that is the volume under cross-correlation plane and autocorrelation of a single nanobubble. The energy of the correlation is agnostic to the displacement patterns and can provide a reliable measurement of object counts.

In Vitro Characterization of the Ultrasound Contrast Agent

To analyze echogenicity and stability of the nanodroplets, diluted nanodroplet solution was added to 150 ml glass beaker and stirred continuously at 150 rpm on a temperature-controlled hotplate (Thermo Scientific) to agitate the nanodroplets. The particles were diluted 1:167.7 with 1×PBS for the repeatability study, and 1:63.5 for the stability and temperature sweep studies. The nanodroplets were imaged using a Vevo 3100 (Fujifilm VisualSonics) preclinical ultrasound imaging system with a MX250 linear array transducer with a center frequency of 21 MHz and an axial resolution of 75 μm. Images were acquired using both B-mode and nonlinear contrast (NLC) mode. The following image acquisition settings were used for the studies: a frequency of 18 MHz, 75% power, a 40 dB dynamic range, a 22 frame per second (fps) acquisition frame rate, a 30 dB gain, and a 30 dB contrast gain. The acquisition depth was set to 9 mm and the focus depth was set to 5 mm. Following each study, the data was exported as MP4 files for image processing and statistical analysis Repeatability of Heat Modulation To evaluate the effect of heat modulation on TDFH nanodroplet echogenicity, thermal modulation process was performed by first heating the dilute nanodroplet solution from room temperature to a setpoint of 42° C.±2° C., and then allowing the solution to cool down to a setpoint of 37° C.±2° C. (n=15). This temperature range was chosen to ensure that we stayed sufficiently below the vaporization threshold of pure TDFH (56° C.). An image series of the droplets (350 frames) was obtained at room temperature (before heat modulation) and at 37° C. (after heat modulation). The data was then exported as MP4 clips for image processing to quantify the effects of thermal modulation. The data was plotted as mean signal intensity values after heat modulation normalized by the average signal intensity before heat modulation. The fold-increase in echogenicity post-treatment was reported as overall mean±STD.

Stability

To determine the signal stability of the nanodroplets after undergoing the heat modulation, nanodroplets were activated via a thermal cycle, and their echogenicity was tracked over the course of 13 hours. A total of 350 frames was recorded for each sample (n=5) at the designated time points (t=0, 1, 2, 3 and 13 hrs), and the normalized signal intensity was plotted as a function of time.

Temperature Sweep

To determine the effect that temperature has on nanodroplet echogenicity, the nanodroplet solution was heated from room temperature to 44° C. and allowed to cool back to room temperature (n=5). The images of the particles were acquired at the following temperature points during the heating and cooling parts of the thermal cycle: 25° C., 28° C., 31° C., 34° C., 37° C., 40° C., 43° C., 44° C. A frame marker was added to the ultrasound clip at each of the designated temperature points. The images were then exported, and the normalized signal intensity was plotted as a function of temperature.

Image Processing

Ultrasound image series were converted to grayscale images, and the boundaries of each individual nanodrop were detected with our developed Matlab code. A three-point Gaussian curve was fitted to the intensity values of each identified nanodrop to find the actual maximum intensity. Next, the maximum intensity of each nanodrop was multiplied by the area of the corresponding nanodrop to get the nanodrop weighted intensity. The intensity level for each frame was then defined as the summation of the nanodrop weighted intensity over all the identified nanodrops. The intensity level was then calculated for all the frames to obtain the intensity level signal for each image series.

Statistical Analysis

All data are presented as mean±standard deviation (STD) unless stated otherwise. Statistical analysis was performed using Minitab 19 software. T-tests were used to determine the significance between experimental groups. Tukey test was performed to derive multiple pairwise statistical comparisons in the stability study.

Results

Nanodroplet Size Distribution and Structural Property

Figure 1:
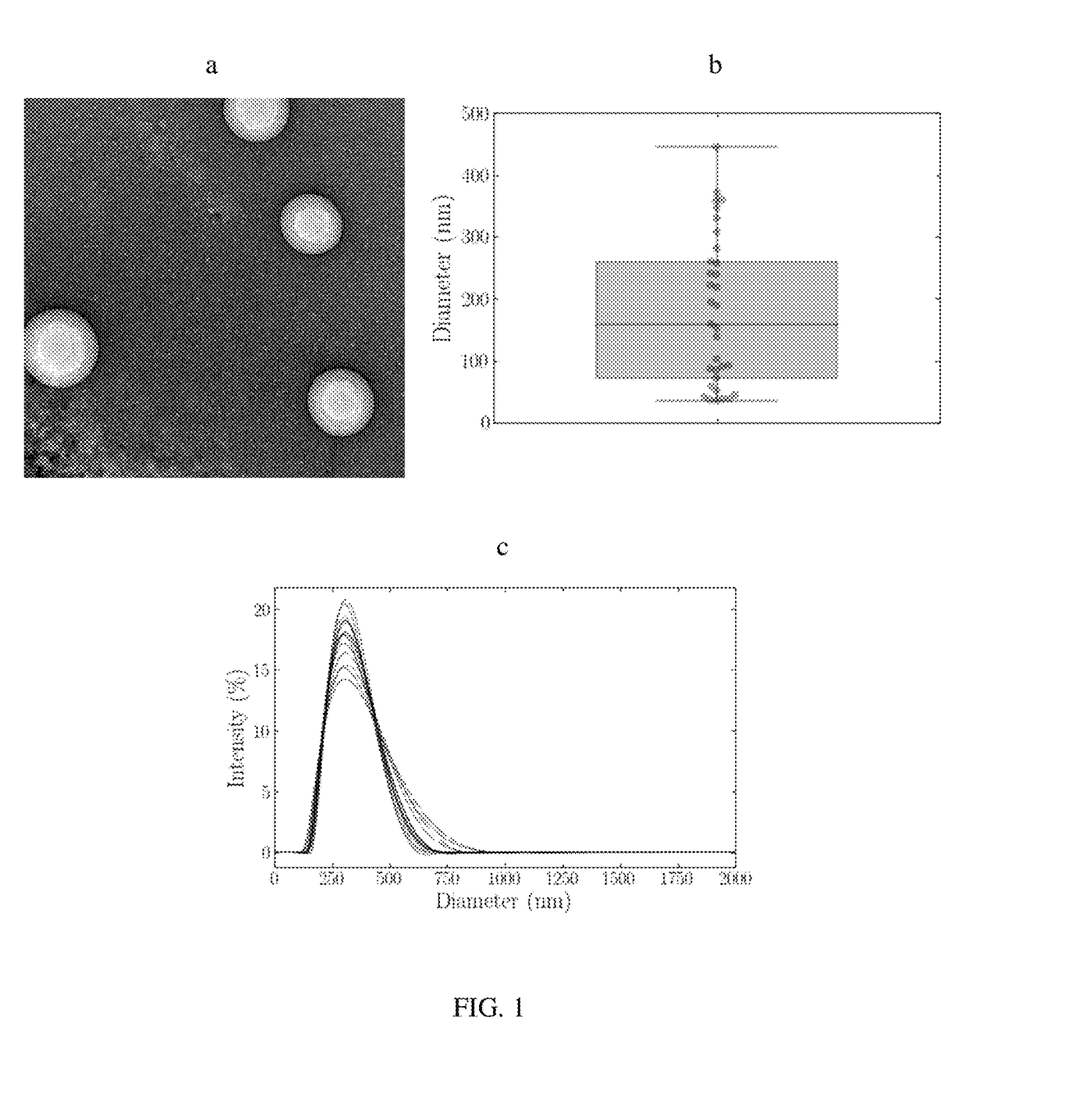
FIG. 1 illustrates internal structure and size of BSA-shelled TDFH nanodroplets. (a) The morphology of BSA-TDFH nanodroplets visualized on the TEM. Scale bar=100 nm. (b) True size distribution of the nanodroplets obtained from TEM images. (c) Size distribution of the nanodroplets obtained by DLS measurements.

TEM was used to show the internal structure of the particles and provide initial information about their true size distribution. TEM images (FIG. 1a) revealed spherical particles with a clearly distinguishable core and surrounding shell. The nanodroplet size distribution obtained from TEM data is presented in FIG. 1b. The average true nanodroplet diameter was 180.2±121.9 nm.

The hydrodynamic diameter of the nanodroplets was then measured using DLS (FIG. 1c). The mean hydrodynamic diameter of the particles was found to be 299.0±3.356 nm with a polydispersity of 0.092±0.030 (n=5). The mean nanodroplet zeta potential was −33.1±1.06 mV (n=5).

In Vitro Heat Modulation: Contrast Enhancement and Repeatability

Figure 2:
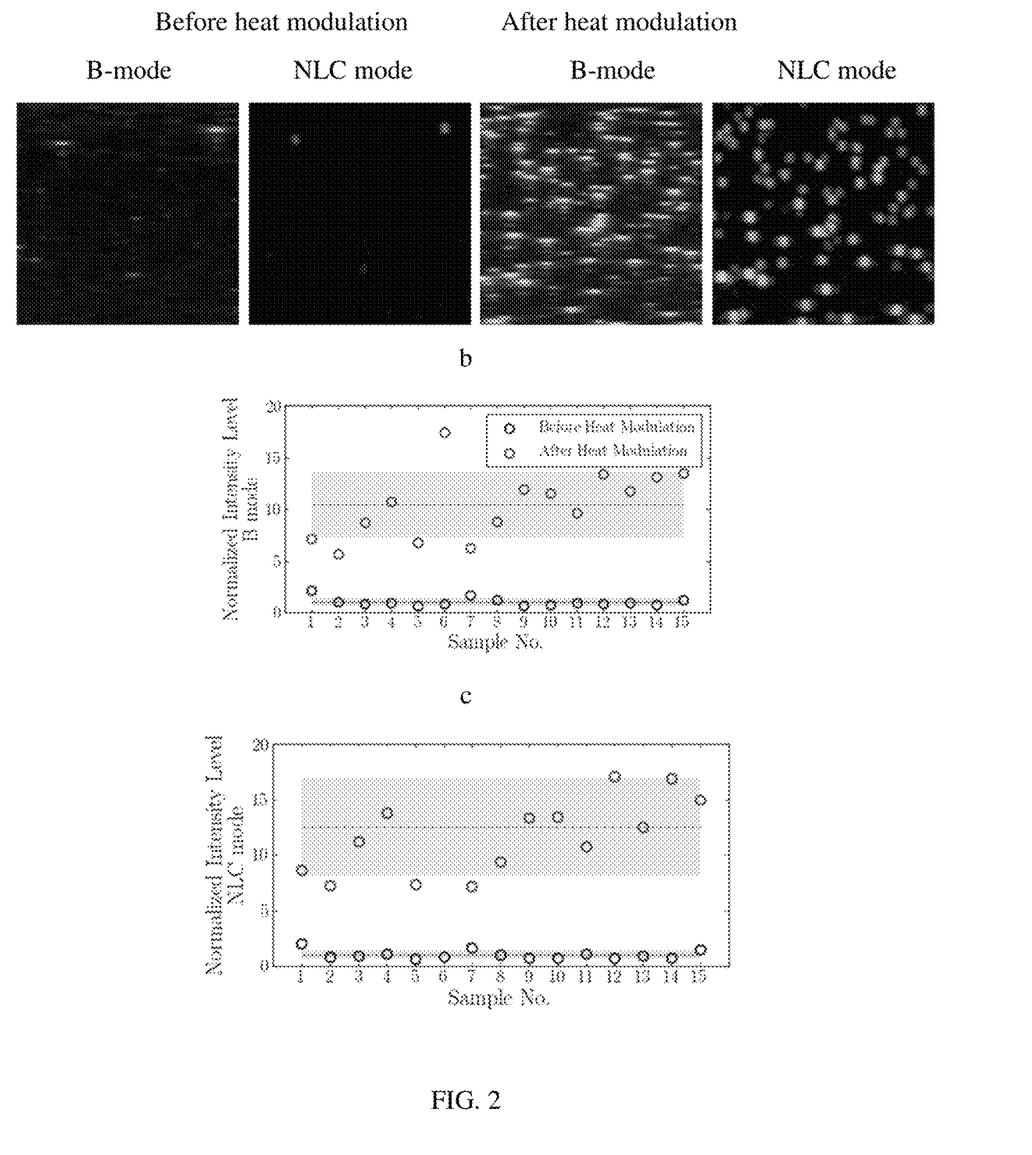
FIG. 2 illustrates analysis of nanodroplet echogenicity before and after thermal modulation. (a) Representative ultrasound images of nanodroplets on the B-mode and the NLC mode before and after heat modulation. (b) Nanodroplet signal intensity on the B-mode before and after heat modulation (n=15). The data was normalized by the grand mean of signal intensity before thermal cycle. (c) Nanodroplet signal intensity on the NLC mode before and after thermal modulation, normalized by the grand mean of signal intensity before treatment.

The ultrasound signal intensity on the B-mode and the nonlinear contrast (NLC) mode before and after heat modulation was quantified to determine the change in signal for the nanodroplets that underwent a thermal cycle (FIG. 2b, 2c). To ensure the validity of the experimental findings, the heat modulation experiment was repeated 15 times, and the ultrasound images were acquired before heat modulation at room temperature and after heat modulation at 37° C.

Figure 3:
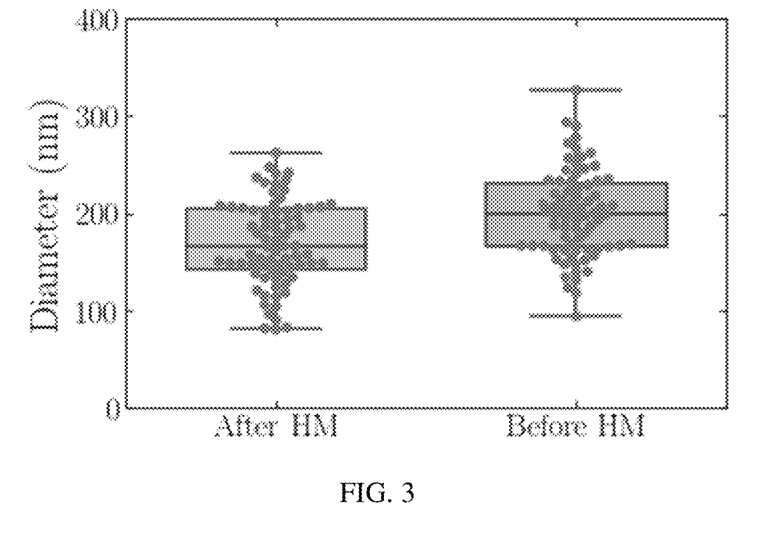
FIG. 3 illustrates size distribution of the nanodroplets obtained by confocal imaging in combination with image-based probability estimation of displacements (iPED) method.

Heat modulation significantly increased the echogenicity of the nanodroplets (p<0.001). The mean fold-increase in nanodroplet echogenicity after the thermal cycle was 10.4±3.3 on the B-mode and 12.5±4.6 on the NLC mode. To determine whether such a significant increase in echogenicity could be attributed to the phase transition of the nanodroplets' TDFH core from liquid to gas and the particles' conversion from nanodroplets to microbubbles, the confocal images of nanodroplets in the microfluidic device were acquired as time series before and after heat modulation (n=5), and the size of particles was determined using the iPED method (FIG. 3). The data showed that both before and after heat modulation, the average diameters of nanodroplets were 199.1±45.0 nm and 169.4±43.3 nm, respectively. The size of the BSA-TDFH nanodroplets after thermal cycle was significantly smaller than before (p<0.001).

Nanodroplet Stability After Heat Modulation

Figure 4:
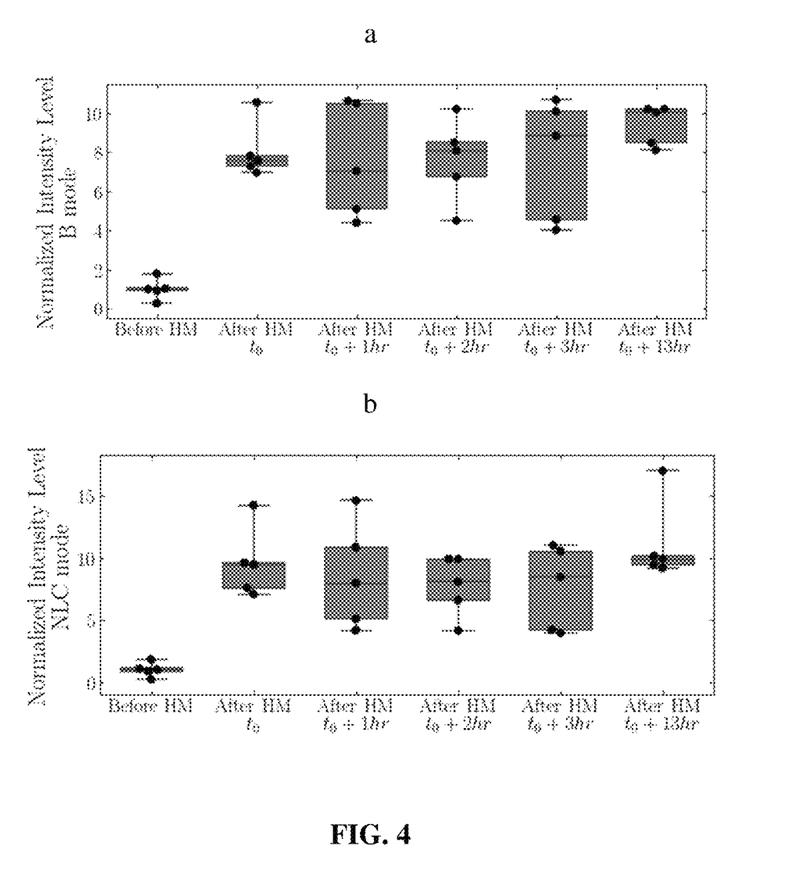
FIG. 4 illustrates analysis of nanodroplet stability. (a) Ultrasound signal intensity on the B-mode as a function of time for 13 h period (n=5). (b) Ultrasound signal intensity on the NLC mode as a function of time over a period of 13 h (n=5).

The echogenicity of thermally-modulated TDFH nanodroplets was monitored for 13 hours post heat activation (FIG. 4a, 4b). The Tukey test for all pairs showed that the mean normalized signal intensity levels at all time points after thermal modulation were significantly different from the mean intensity level before modulation, but not statistically different from each other. Therefore, the data showed that the particles were stable and, once activated, retained their enhanced signal for 13 hours.

Nanodroplet Echogenicity Changes as a Function of Temperature

Figure 5:
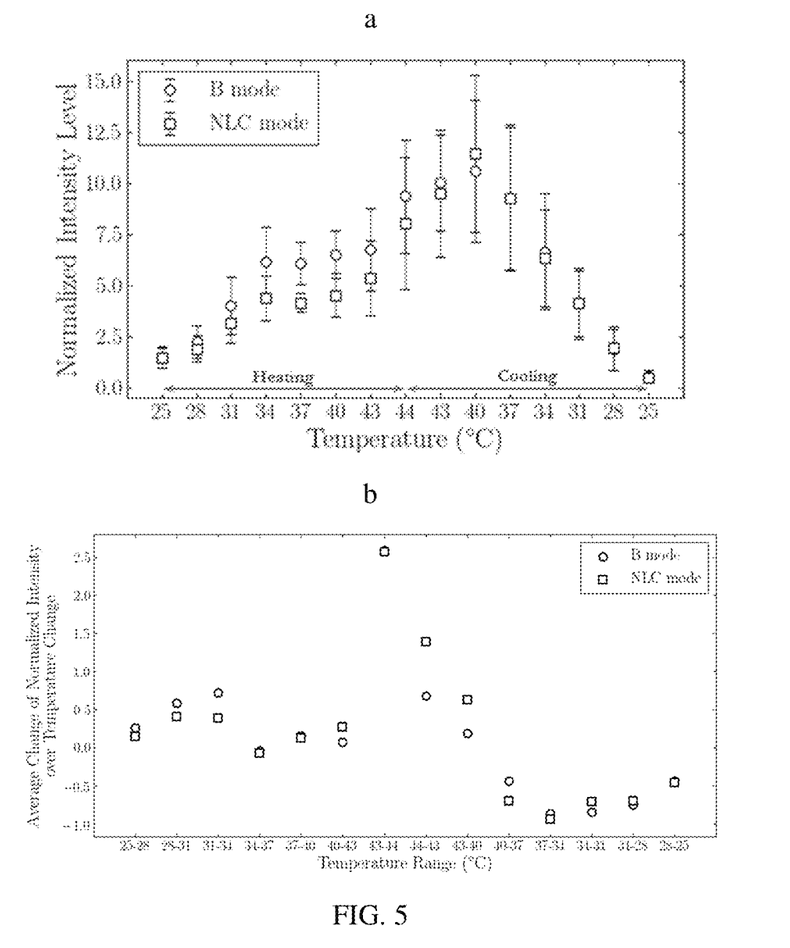
FIG. 5 illustrates analysis of thermally-responsive nanodroplet behavior. (a) Nanodroplet signal intensity as a function of temperature on the B-mode and the NLC mode (n=5). The data was normalized by the mean signal intensity at 25° C. (b) The mean rate of change of nanodroplet echogenicity with respect to temperature plotted over selected temperature intervals.
Figure 6:
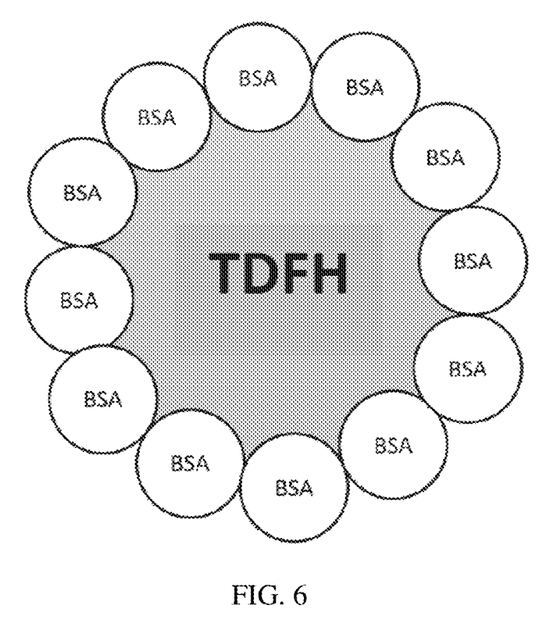
FIG. 6 illustrates a BSA-shelled tetradecafluorohexane nanodroplet.

As shown in FIG. 5a, nanodroplet echogenicity displays thermally dependent behavior over a selected range of temperatures. The nanoparticle signal intensity increased with increasing solution temperature and decreased back to the baseline value as the nanodroplet solution was cooled back down to 25° C. However, the nanodroplet echogenicity showed a delayed response after reaching the peak temperature of 44° C.: the mean rate of change of nanodroplet signal intensity with respect to temperature had a sharp increase on the temperature interval from 43° C. to 44° C. and continued to be positive over the 44° C.–43° C. and 43° C.–40° C. temperature ranges (FIG. 5b). As a result, the highest nanoparticle echogenicity during the thermal cycle was recorded not at the peak temperature of 44° C., but at 40° C. during the cooling portion of the cycle. Nanodroplets had higher signal intensity at 37° C. during the cooling period compared to when they first reached that temperature in the heating part of the thermal sweep. Therefore, higher echogenicity of BSA-TDFH nanodroplets was induced with thermal modulation compared to direct heating to 37° C.

Discussion

This study demonstrates that BSA-TDFH nanodroplets exhibit unforeseen temperature-sensitive echogenic behavior that is independent of droplet vaporization, and show the efficacy of thermal modulation as a novel method to induce echogenicity of PFC nanodroplets with typically negligible acoustic contrast properties.

The data presented in this study revealed that the mean nanodroplet size varied depending on the type of diameter being measured (true versus hydrodynamic) and the sizing method being used but was below 310 nm in all cases. This indicates that the particles are small enough to exit the "leaky" vasculature of the tumors that features open pores ranging in size from 380 nm to 780 nm. Therefore, the nanodroplets could potentially be used for extravascular ultrasound imaging, given that they provide enough contrast enhancement.

This disclosure showed that the echogenicity of TDFH nanodroplets was enhanced without a transient phase change of the liquid core by heat modulation, i.e. subjecting the particle solution to a heating and cooling cycle. The method proved to be effective as it induced a mean-fold increase of 10.4±3.3 in nanodroplet signal intensity on the B-mode and 12.5±4.6 on the NLC mode. The size of the nanodroplets did not increase after heat modulation, supporting that the enhanced echogenicity was not caused by volumetric expansion of the particles typical for the cases of ADV. This was expected, as the heating range for heat modulation experiments (room temperature—44° C.) was far below the vaporization temperature of pure liquid TDFH (56° C.). Statistical analysis showed that the nanodroplet size after thermal cycle was significantly smaller than before. Although we used a heated confocal chamber to keep thermally-modulated nanodroplets at 37° C. during image acquisition, it is possible that the actual temperature inside the chamber was slightly off from the setpoint, which would have affected the size calculations. Minor changes in the solution viscosity with increased temperature could have played a role as well.

The echogenicity of BSA-shelled TDFH nanodroplets was temperature-sensitive, and the signal intensity generally increased with increasing temperature and declined with decreasing temperature. However, the rate of change of nanodroplet echogenicity with respect to temperature remained positive for some time after the particle solution reached the peak temperature. We were particularly interested in the nanodroplet behavior at the normal core body temperature of 37° C. interestingly, the nanoparticles at 37° C. during the cooling part of the thermal cycle were more echogenic compared to when they first reached that same temperature during the heating portion of the thermal sweep. Therefore, thermal modulation yields more echogenic particles than direct heating to 37° C.

After undergoing heat modulation, the nanodroplets exhibited echogenic stability in vitro and retained their enhanced echogenicity over the course of 13 hours. Some fluctuations in signal intensity were observed over time, likely due to the solution temperature oscillating around the setpoint and thus affecting the echogenicity of the particles. No decay in signal intensity was observed throughout the stability study and at t=13 hrs. This stability of thermally-modulated TDFH nanodroplets could be very beneficial for tumor imaging and therapeutic applications of ultrasound, and should be explored in the future research.

The results presented in this disclosure suggest that thermal modulation is a novel effective method for inducing echogenicity of BSA-TDFH nanodroplets that, in contrast to ADV, preserves the nanoscale size of the particles and their echogenic stability. Up to date, the application of PFC nanodroplets in their unaltered state in US imaging and US-mediated therapies has been limited due to their weak echogenic properties. However, the technology presented here has the potential to help significantly expand the range of applications of stable nanodroplets in diagnostic and therapeutic ultrasound.

This disclosure study presents the results of a discovery that the echogenicity of protein-shelled TDFH nanodroplets exhibits unexpected thermal responsiveness over a temperature range below the phase transition temperature of pure TDFH. Based on these experimental findings, a novel thermal modulation method for controlled, vaporization-independent activation of the liquid-based ultrasound contrast agent was developed. This simple yet effective method induced echogenicity of traditionally poorly echogenic PFC-based nanodroplets while preserving their nanoscale size and stability. Thermally-modulated BSA-TDFH nanodroplets showed more than a tenfold increase in echogenicity, on average, and maintained the enhanced signal for 13 hours.

We claim:

1. A nano-droplet composition comprising a fluorocarbon core and a polymeric shell, wherein:
    the fluorocarbon core and the polymeric shell form a micelle with a size range of 10-1000 nm;
    the fluorocarbon core comprises at least one fluorocarbon compound with a formula of $C_nF_{2n+2}$ and n is 5-10;
    the polymeric shell comprises a biocompatible polymic material, wherein the biocompatible polymeric material comprises bovine serum albumin and is modified with various ligands to turn the nano-droplet into a multi-functional agent suitable for targeted diagnostics and therapy;
    the fluorocarbon compound is substantial in liquid form; and
    the nano-droplet composition has a temperature profile such that the nano-droplet composition has a temperature range of 20-60° C. throughout a temperature modulation process, and has a temperature of about 37° C. prior to administration to a human, animal, biological cell, or tissue subject.

2. The composition of claim 1, wherein the fluorocarbon compound is perfluorohexane ($C_6F_{14}$).

3. The composition of claim 1, wherein the fluorocarbon core comprises at least 90 wt. % of fluorocarbon.

4. The composition of claim 1, wherein the nano-droplet composition is used as an ultrasound contrast agent in an ultrasound imaging process.

5. The composition of claim 4, wherein the nano-droplet micelle maintains a size range between 10-1000 nm and the fluorocarbon compound maintains the liquid form throughout temperature modulation process and the ultrasound imaging process.

6. The composition of claim 4, wherein the nano-droplet composition can provide sufficient ultrasound contrast function for at least 10 minutes.

7. The composition of claim 6 wherein the nano-droplet composition can provide sufficient ultrasound contrast function for 30-780 minutes.

8. The composition of claim 1, wherein the biocompatible polymeric material further comprises polysaccharides, lipids, nucleic acids, or any combination thereof.

9. A method of using a nano-droplet composition as an ultrasound contrast agent, wherein the method comprises:
providing a nano-droplet composition comprising a core and a polymeric shell, wherein the fluorocarbon core and a polymeric shell forms a micelle with a size range of 10-1000 nm, wherein the polymeric shell comprises a biocompatible polymeric material, wherein the biocompatible polymeric material comprises bovine serum albumin, alone or in further combination with a synthetic polymer, a polysaccharide, a protein, a peptide, a lipid, a nucleic acid, or any combination thereof; and wherein the core is substantial in liquid form;
subjecting the nano-droplet composition to a temperature modulation process to modulated or enhance the ultrasound signal exhibited by the nano-droplet composition, wherein the temperature modulation process is applied outside a human, animal or biological cell or tissue for an ultrasound imaging process and can be controlled;
administering the nano-droplet composition that exhibits enhanced ultrasound contrast to the human, animal or biological cell or tissue subject; and
performing an ultrasound imaging on the human, animal or biological cell or tissue.

10. The method of claim 9, wherein the nano-droplet composition has a temperature profile such that the nano-droplet composition has a temperature range of 20-60° C. throughout a temperature modulation process, and has a temperature of about 37° C. prior to administration to a human, animal, biological cell, or tissue.

11. The method of claim 9, wherein the core comprises at least one fluorocarbon compound, wherein the fluorocarbon compound has a formula of $C_nF_{2n+2}$ and n is 5-10; and wherein the fluorocarbon compound is substantial in liquid form.

12. The method of claim 11, wherein the fluorocarbon compound is perfluorohexane ($C_6F_{14}$).

13. The method of claim 9, wherein the nano-droplet composition can provide sufficient ultrasound contrast function for at least 10 minutes.

14. The method of claim 9, wherein the nano-droplet composition can provide sufficient ultrasound contrast function for 30-780 minutes.

15. The method of claim 9, wherein the temperature modulation process comprises a cycle of elevating temperature of the nano-droplet composition above 37° C. first, and cooling temperature to 37° C. or any other temperature below 37° C.

16. The method of claim 15, wherein the temperature modulation process comprises a plurality of cycles of elevating and cooling the temperature of the nano-droplet composition to allow the nano-droplet composition to have an optimized external temperature profile as an ultrasound contrast agent.

17. A nano-droplet compositioon comprising a fluorocarbon core and a polymeric shell, wherein:
the fluorocarbon core and the polymeric shell form a micelle with a size range of 10-1,000 nm:
the fluorocarbon core comprises at least one fluorocarbon compound with a formula of $C_nF2_{n+2}$ and n is 5-10;
the polymeric shell comprises a biocompatible polymeric material, wherein the biocompatible polymeric mterial comprises bovine serum albumin, alone or in further combination with a polysaccharide, a protein, a peptide, a lipid, a nucleic acid, or any combination thereof, and is optionally modified with various ligands to turn the nano-droplet into a multi-functional agent suitable for targeted diagnostics and therapy;
the fluorocarbon compound is substantially in liquid form; and
wherein the nano-droplet composition has enhance echogenicity in the absence of a transient or complete phase change of the fluorocarbon core from being subjected to a controlled temperature modulation process.

18. The nano-droplet composition of claim 17, wherein the controlled temperature modulation process comprises subjecting the nano-droplet composition to a cycle of elevating temperature above 37° C. and cooling temperature to 37° C. or below.

19. A nano-droplet composition comprising a fluorocarbon core and a polymeric shell, wherein:
the fluorocarbon core and the polymeric shell form a micelle with a size range of 10-1,000 nm;
the fluorcarbon core comprises at least one fluorocarbon compound with a formula of $C_nF_{2n+2}$ and n is 5-10;
the polymeric shell comprises a biocompatible polymeric material, wherein the biocompatible polymeric material comprises bovine serum albumin, alone or in further combination with a synthetic polymer, a polysaccharide, a protein, a pepetide, a lipid, a nucleic acid, or any combination thereof, and is optionally modified with various ligands to turn the nano-droplet into a multi-functional agent suitable for targeted diagnostics and therapy;
the fluorocarbon compound is substantially in liquid form; and
wherein the nano-droplet composition has enhance echogenicity in the absence of a transient phase change of the fluorocarbon core from being subjected to a controlled temperature modulation process.

20. The nano-droplet composition of claim 19, wherein the controlled temperature modulation process comprises subjecting the nano-droplet composition to a cycle of elevating temperature above 37° C. and cooling temperature to 37° C. or below.

* * * * *